(12) United States Patent
Scholz et al.

(10) Patent No.: US 8,709,069 B2
(45) Date of Patent: Apr. 29, 2014

(54) FLANGED GRAFT WITH TRIM LINES (75) Inventors: Hans Scholz, Berlin (DE); John D. McDermott, Chandler, AZ (US); Robert M. Carr, Jr., Paradise Valley, AZ (US); Debra A. Bebb, Mesa, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 2064 days.

(21) Appl. No.: 11/408,330

(22) Filed: Apr. 21, 2006

(65) Prior Publication Data

US 2007/0005128 A1    Jan. 4, 2007

Related U.S. Application Data (60) Provisional application No. 60/695,406, filed on Jul. 1, 2005.

(51) Int. Cl.
*A61F 2/06* (2013.01)
(52) U.S. Cl.
USPC .......................................... 623/1.36; 606/153
(58) Field of Classification Search
USPC ........................... 606/155; 623/1.3, 1.31, 1.36
See application file for complete search history.

(56) References Cited

U.S. PATENT DOCUMENTS

| | | |
|---|---|---|
| 2,127,903 A | 8/1938 | Bowen |
| 3,196,194 A | 7/1965 | Ely, Jr. et al. |
| 3,492,994 A | 2/1970 | Field |
| 3,683,926 A | 8/1972 | Suzuki |
| 3,713,441 A | 1/1973 | Thomas |
| 3,805,301 A | 4/1974 | Liebig |
| 3,816,919 A | 6/1974 | Portnoy |
| 3,818,511 A | 6/1974 | Goldberg et al. |
| 3,825,257 A | 7/1974 | Palmer |
| 3,853,462 A | 12/1974 | Smith |
| 3,882,862 A | 5/1975 | Berend |
| 3,945,052 A | 3/1976 | Liebig |
| 3,986,828 A | 10/1976 | Loffman, Jr. et al. |
| 4,047,252 A * | 9/1977 | Liebig et al. ................ 623/1.52 |
| 4,098,571 A | 7/1978 | Miyata et al. |
| 4,192,312 A | 3/1980 | Wilson |
| 4,234,535 A | 11/1980 | Okita |

(Continued)

FOREIGN PATENT DOCUMENTS

| | | |
|---|---|---|
| EP | 0269254 | 10/1987 |
| JP | 63158052 | 7/1988 |

(Continued)

OTHER PUBLICATIONS

Batson, R.C., M.D. et al.; "Linton Patch Angioplasty", Ann. Surg, Jun. 1984.

(Continued)

*Primary Examiner* — David Isabella
*Assistant Examiner* — Ann Schillinger
(74) *Attorney, Agent, or Firm* — Rutan & Tucker, LLP (57) ABSTRACT

A vascular graft with trim lines is described, the trim lines providing a guide for precision shaping of the cuff. The trim lines may be printed or otherwise disposed on a surface of the cuff or included on a template designed for disposition over the cuff. The trim lines may also be disposed on a side of a pocket into which the cuff is positioned for trimming. Also described is an apparatus and method for precise trimming of a vascular graft.

14 Claims, 4 Drawing Sheets

(56) References Cited

U.S. PATENT DOCUMENTS

| | | |
|---|---|---|
| 4,279,259 A | 7/1981 | Lee et al. |
| 4,309,776 A | 1/1982 | Berguer |
| 4,313,231 A | 2/1982 | Koyamada |
| 4,321,914 A | 3/1982 | Begovac et al. |
| 4,345,414 A | 8/1982 | Bornat et al. |
| 4,354,495 A | 10/1982 | Bodicky |
| 4,366,819 A | 1/1983 | Kaster |
| 4,387,516 A * | 6/1983 | Laux .................................. 36/43 |
| 4,416,028 A | 11/1983 | Eriksson et al. |
| 4,441,215 A | 4/1984 | Kaster |
| 4,482,516 A | 11/1984 | Bowman et al. |
| 4,501,263 A | 2/1985 | Harbuck |
| 4,503,568 A | 3/1985 | Madras |
| 4,517,687 A | 5/1985 | Liebig et al. |
| 4,530,113 A | 7/1985 | Matterson |
| 4,601,718 A | 7/1986 | Possis et al. |
| 4,630,375 A | 12/1986 | Spolyar |
| 4,712,551 A | 12/1987 | Rayhanabad |
| 4,714,421 A | 12/1987 | D'Agostino |
| 4,728,328 A | 3/1988 | Hughes et al. |
| 4,743,480 A | 5/1988 | Campbell et al. |
| 4,807,622 A | 2/1989 | Ohkaka et al. |
| 4,816,028 A | 3/1989 | Kapadia et al. |
| 4,840,940 A | 6/1989 | Sottiurai |
| 4,872,455 A | 10/1989 | Pinchuk et al. |
| 4,883,453 A | 11/1989 | Berry et al. |
| 4,909,979 A | 3/1990 | Possis et al. |
| 4,935,190 A | 6/1990 | Tennerstedt |
| 4,944,737 A | 7/1990 | Bloom |
| 4,957,508 A | 9/1990 | Kaneko et al. |
| 4,957,669 A | 9/1990 | Primm |
| 5,042,161 A * | 8/1991 | Hodge ....................... 33/501.45 |
| 5,078,735 A | 1/1992 | Mobin-Uddin |
| 5,100,422 A | 3/1992 | Berguer et al. |
| 5,110,526 A | 5/1992 | Hayashi et al. |
| 5,156,619 A | 10/1992 | Ehrenfeld |
| 5,304,340 A | 4/1994 | Downey |
| D348,618 S | 7/1994 | Leslie et al. |
| 5,376,110 A | 12/1994 | Tu et al. |
| 5,387,236 A | 2/1995 | Noshiki et al. |
| 5,399,352 A | 3/1995 | Hanson |
| 5,443,497 A | 8/1995 | Vendrux |
| 5,456,712 A | 10/1995 | Maginot |
| 5,456,714 A | 10/1995 | Owen |
| 5,472,404 A | 12/1995 | Volgushev |
| 5,476,506 A | 12/1995 | Lunn |
| 5,496,341 A | 3/1996 | Sauer et al. |
| 5,500,014 A | 3/1996 | Quijano et al. |
| 5,575,817 A | 11/1996 | Martin |
| 5,591,203 A | 1/1997 | Fahy |
| 5,653,743 A | 8/1997 | Martin |
| 5,683,449 A | 11/1997 | Marcade |
| 5,695,504 A | 12/1997 | Gifford, III et al. |
| 5,713,859 A | 2/1998 | Finch, Jr. et al. |
| 5,723,005 A | 3/1998 | Herrick |
| 5,752,934 A | 5/1998 | Campbell et al. |
| 5,755,779 A | 5/1998 | Horiguchi |
| 5,755,780 A | 5/1998 | Finch, Jr. et al. |
| 5,782,916 A | 7/1998 | Pintauro et al. |
| 5,824,010 A | 10/1998 | McDonald |
| 5,827,327 A | 10/1998 | McHaney et al. |
| 5,843,158 A | 12/1998 | Lenker et al. |
| 5,843,165 A | 12/1998 | Plaia et al. |
| 5,849,036 A | 12/1998 | Zarate |
| 5,861,026 A | 1/1999 | Harris et al. |
| 5,893,886 A | 4/1999 | Zegdi et al. |
| 5,902,317 A | 5/1999 | Kleshinski et al. |
| 5,950,320 A | 9/1999 | Dorsey |
| 5,976,159 A | 11/1999 | Bolduc et al. |
| 5,989,287 A | 11/1999 | Yang et al. |
| 6,019,788 A | 2/2000 | Butteres et al. |
| 6,039,754 A | 3/2000 | Caro |
| 6,048,362 A * | 4/2000 | Berg .......................... 623/1.34 |
| 6,056,717 A | 5/2000 | Finch et al. |
| 6,086,553 A | 7/2000 | Akbik |
| 6,102,884 A | 8/2000 | Squitieri |
| 6,136,022 A | 10/2000 | Nunez |
| 6,187,033 B1 | 2/2001 | Schmitt et al. |
| 6,190,590 B1 | 2/2001 | Randall et al. |
| 6,193,746 B1 | 2/2001 | Strecker |
| 6,203,735 B1 | 3/2001 | Edwin et al. |
| 6,210,430 B1 | 4/2001 | Solem |
| 6,221,101 B1 | 4/2001 | Harris et al. |
| 6,273,912 B1 * | 8/2001 | Scholz et al. ................. 623/1.31 |
| 6,371,981 B1 | 4/2002 | Yang et al. |
| 6,436,135 B1 | 8/2002 | Goldfarb |
| 6,458,155 B1 * | 10/2002 | Van Nguyen et al. ........ 623/2.11 |
| 6,554,856 B1 | 4/2003 | Doorly et al. |
| 6,582,409 B1 | 6/2003 | Squitieri |
| 6,585,762 B1 | 7/2003 | Stanish |
| 6,589,278 B1 | 7/2003 | Harris et al. |
| 6,613,087 B1 * | 9/2003 | Healy et al. .................. 623/2.14 |
| 6,626,865 B1 | 9/2003 | Prisell |
| 6,626,939 B1 * | 9/2003 | Burnside et al. ............. 623/1.38 |
| 6,746,480 B2 | 6/2004 | Scholtz et al. |
| 6,767,358 B2 | 7/2004 | Leonhardt et al. |
| 6,821,295 B1 | 11/2004 | Farrar |
| 6,857,196 B2 | 2/2005 | Dalrymple |
| 6,858,035 B2 | 2/2005 | Whayne |
| 7,553,316 B2 | 6/2009 | Scholz et al. |
| 2002/0193872 A1 | 12/2002 | Trout et al. |
| 2003/0014108 A1 | 1/2003 | Lauren |
| 2003/0051362 A1 | 3/2003 | Buckman et al. |
| 2003/0182815 A1 | 10/2003 | Carlson |
| 2004/0039453 A1 * | 2/2004 | Anderson et al. .......... 623/23.72 |
| 2004/0064181 A1 | 4/2004 | Harris et al. |
| 2004/0210302 A1 | 10/2004 | Scholz et al. |
| 2005/0055079 A1 | 3/2005 | Duran |
| 2005/0272806 A1 | 12/2005 | Falotico et al. |
| 2006/0030935 A1 | 2/2006 | Scholz et al. |
| 2006/0210816 A1 | 9/2006 | Finley |
| 2007/0255400 A1 | 11/2007 | Parravicini et al. |
| 2010/0280598 A1 | 11/2010 | Fox |

FOREIGN PATENT DOCUMENTS

| | | |
|---|---|---|
| WO | 9509585 A1 | 4/1995 |
| WO | 9514442 | 6/1995 |
| WO | 9534255 A1 | 12/1995 |
| WO | WO 96/00103 | 1/1996 |
| WO | WO 97/31591 | 9/1997 |
| WO | WO 98/52495 | 11/1998 |

OTHER PUBLICATIONS

Bard Peripheral Vascular, Inc.; "Hemodynamics and Cuff Technology" (2005).
Bard Peripheral Vascular, Inc., "Venaflo Vascular Grafts Information for Use", Rev. 2, Oct. 2004.
Beard, J.D. et al., "Haemodynamics of the Interposition Vein Cuff", Br. J. Surg, vol. 73, No. 10, pp. 823-825, Oct. 1986.
Chester et al., "Interposition Vein Patches for Vascular Reconstruction", pp. 1-3.
Crawshaw et al., "Flow Disturbance at the Distal End-to-Side Anastomosis", Arch Surg, vol. 115, pp. 1280-1284, Nov. 1980.
da Silva, A.F. et al., "Stable Vortices Within Vein Cuffs Inhibit Anastomotic Myointimal Hyperplasia", Eur J Vasc Surg, vol. 14, pp. 157-163 (1997).
Dobrin et al., "Mechanical factors predisposing to intimal hyperplasia and medial thickening in autogenous vein grafts", Surgery, vol. 105, No. 3, pp. 393-400, Mar. 1989.
Escobar, Francisco S. III et al., "Comparison of a New Hooded Graft With a Conventional ePTFE Graft: A Preliminary Study", Vascular Access for Hemodialysis VI, pp. 205-212 (1999).
Fillinger et al., "Beneficial Effects of Banding on Venous Intimal-Medial Hyperplasia in Arteriovenous Loop Grafts"; The American Journal of Surgery, vol. 158, pp. 87-94, Aug. 1989.
Fillinger et al., "Graft Geometry and Venous Intimal-Medial Hyperplasia in Arteriovenous Loop Grafts", Journal of Vascular Surgery, vol. 11, No. 4, pp. 556-566., Apr. 1990.

(56) References Cited

OTHER PUBLICATIONS

Fisher, R.K. et al., "Harnessing Haemodynamic Forces for the Suppression of Anastomotic Intimal Hyperplasia: the Rationale for Precuffed Grafts", Eur J Vasc Endovasc Surg, vol. 21, pp. 520-528 (2001).
Gagne, P. J. et al., "The Effect of a Venous Anastomosis Tyrell Vein Collar on the Primary Patency of Arteriovenous Grafts in Patients Undergoing Hemodialysis", J Vasc Surg, vol. 32, No. 6 (2000).
Green, R. M. et al., "Prosthetic Above-Knee Femoropopliteal Bypass Grafting: Five-Year Results of a Randomized Trial", J Vasc Surg, vol. 31, No. 3, Mar. 2000.
Harris, Peter et al., "Haemodynamics of Cuffed Arterial Anastomoses", Critical Ischaemia, vol. 9, No. 1, pp. 20-26 (1999).
How, T.V., PhD et al., "Interposition Vein Cuff Anastomosis Alters Wall Shear Stress Distribution in the Recipient Artery", J Vasc Surg, vol. 31, No. 5, May 2000.
Impra, Inc., "Suturing Technique for Venaflo ePTFE Vascular Graft & Venaflo Graft with Carbon" (1998).
Impra, Inc., "Tunneling Technique for Venaflo ePTFE Vascular Graft & Venaflo Graft with Carbon" (1999).
Jamieson, et al, "Vascular Surgery", 5th Ed., pp. 330-340 (1994).
Krueger et al., "Importance of Correct Trimming of Venaflo Grafts Proven by CFD", 4th International Congress of the Vascular Access Society, Berlin, Germany, May 25, 2005.
Lei, Ming PhD et al., "Computational Design of a Bypass Graft That Minimizes Wall Shear Stress Gradients in the Region of the Distal Anastomosis", Journal of Vascular Surgery, vol. 25, No. 4, pp. 637-646, Apr. 1997.
Lemson, M.S. et al., "effects of a Venous Cuff at the Venous Anastomosis of Polytetrafluoroethylene Grafts for Femodialysis Vascular Access", J Vasc Surg, vol. 32, No. 6, Dec. 2000.
Loh, A. et al., "PTFE Bypass Grafting to Isolated Popliteal Segments in Critical Limb Ischaemia", Eur J Vasc Surg, vol. 7, pp. 26-30, Jan. 1993.
Miller et al., "Use of the Vein Cuff and PTFE", Vascular Surgical Techniques an Atlas, Second Edition, pp. 276-286.
Nyberg et al., "Preliminary Experience with a Cuffed ePTFE Graft for Hemodialysis Vascular Access", Asaio Journel, vol. 47, No. 4, Jul./Aug. 2001.
Panneton, J. M., MD., Multicenter Randomized Prospective Trial Comparing a Pre-Cuffed Polytetrafluoroethylene Graft to a Vein Cuffed Polytetrafluoroethylene Graft for Infragenicular Arterial Bypass, Ann Vasc Surg, vol. 18, pp. 199-206, Mar. 15, 2004.
Queen Elisabeth Hospital Berlin, "Documentation of Comparative Flow Investigations of the Conventional Anastomosis and 'Venaflo II' Anastomosis by a Pulsatile Curculating Model".
Scholz, Hans M.D. et al., "Five Years' Experience With an Arteriovenous Patch Prosthesis as Access for Hemodialysis", Vascular Access for Hemodialysis VI, pp. 241-254 (1999).
Sivanesan, S. et al., "Flow Patterns in the Radiocephalic Arteriovenous Fistular: An in Intro Study", J Biomech, vol. 32, pp. 915-925 (1999).
Sorom, A.J. et al., "Prospective, Randomized Evaluation of a Cuffed Expanded Polytetrafluoroethylene Graft for Hemodialysis Vascular Access", Surgery, vol. 132, No. 2, Aug. 2002.
Stonebridge, P.A. et al., "Randomized Trial Comparing Infrainguinal Polytetrafluoroethylene Bypass Grafting With and Without Vein Interpostion Cuff at the Distal Anastomosis", J Vasc Surg, 26(4),pp. 543-550, Oct. 1997.
Taylor et al., "Improved Technique for Polytetraflouroethylene Bypass Grafting: Long-Term Results Using Anastomotic Vein Patches", The British Journal of Surgery, 1992, vol. 79, pp. 348-354, Apr. 4, 1992.
Tyrrell, M.R. et al, "New Prosthetic Venous Collar Anastomotic Technique: Combining the Best of Other Procedures", Br J Surg, vol. 78, pp. 1016-1017, Aug. 1991.
Wells et al., "Effect of carotid artery geometry on the magnitude and distribution of wall shear stress gradients", Journal of Vascular Surgery, vol. 23, No. 4, pp. 667-678, Apr. 1996.
Wolfe, John H. N.; "Polytetrafluoroethylene (PTFE) Femorodistal Bypass", Rob & Smith's Operative SurgeryNascular Surgery Fifth Edition, pp. 330-340.
Advertisement for FEP-Ringed GORE-TEX Vascular Graft, 1 page, prior to Jun. 21, 1989.
EP 98921634.6 filed May 15, 2008 Office Action dated May 5, 2004.
EP 98921634.6 filed May 15, 2008 Office Action dated Oct. 10, 2004.
PCT/GB1998/001418 filed May 15, 1998 International Preliminary Examination Report dated Aug. 25, 1999.
PCT/GB1998/001418 filed May 15, 1998 Written Opinion dated Sep. 2, 1998.
U.S. Appl. No. 10/603,952, filed Jun. 25, 2003 Advisory Action dated Dec. 3, 2010.
U.S. Appl. No. 10/603,952, filed Jun. 25, 2003 Advisory Action dated Jun. 8, 2006.
U.S. Appl. No. 10/603,952, filed Jun. 25, 2003 Advisory Action dated Sep. 4, 2007.
U.S. Appl. No. 10/603,952, filed Jun. 25, 2003 Final Office Action dated Apr. 16, 2007.
U.S. Appl. No. 10/603,952, filed Jun. 25, 2003 Final Office Action dated Feb. 17, 2006.
U.S. Appl. No. 10/603,952, filed Jun. 25, 2003 Final Office Action dated Oct. 18, 2004.
U.S. Appl. No. 10/603,952, filed Jun. 25, 2003 Final Office Action dated Sep. 16, 2010.
U.S. Appl. No. 10/603,952, filed Jun. 25, 2003 Non-Final Office Action dated Apr. 22, 2004.
U.S. Appl. No. 10/603,952, filed Jun. 25, 2003 Non-Final Office Action dated Apr. 6, 2010.
U.S. Appl. No. 10/603,952, filed Jun. 25, 2003 Non-Final Office Action dated Aug. 31, 2006.
U.S. Appl. No. 10/603,952, filed Jun. 25, 2003 Non-Final Office Action dated Mar. 4, 2005.
U.S. Appl. No. 10/603,952, filed Jun. 25, 2003 Non-Final Office Action dated Oct. 15, 2009.
PCT/GB1998/001418 filed May 15, 1998 International Search Report dated Sep. 2, 1998.
JP 2006-303732 Office Action dated Jun. 2, 2009.
PCT/US2008/088312 filed Dec. 24, 2008 Search Report dated Feb. 13, 2009.
PCT/US2008/088312 filed Dec. 24, 2008 Written Opinion dated Feb. 13, 2009.
U.S. Appl. No. 10/603,952, filed Jun. 25, 2003 Non-Final Office Action dated May 10, 2013.
U.S. Appl. No. 10/603,952, filed Jun. 25, 2003 Decision on Appeal dated Jan. 16, 2013.
U.S. Appl. No. 10/842,582, filed May 10, 2004 Final Office Action dated Dec. 31, 2008.
U.S. Appl. No. 10/842,582, filed May 10, 2004 Non-Final Office Action dated Jul. 5, 2007.
U.S. Appl. No. 10/842,582, filed May 10, 2004 Non-Final Office Action dated Nov. 16, 2007.
U.S. Appl. No. 11/239,416, filed Sep. 30, 2005 Final Office Action dated Mar. 25, 2010.
U.S. Appl. No. 11/239,416, filed Sep. 30, 2005 Non-Final Office Action dated Jun. 7, 2013.
U.S. Appl. No. 11/239,416, filed Sep. 30, 2005 Non-Final Office Action dated Sep. 18, 2009.
U.S. Appl. No. 12/810,822, filed Jun. 25, 2010 Final Office Action dated Sep. 28, 2012.
U.S. Appl. No. 12/810,822, filed Jun. 25, 2010 Non-Final Office Action dated Apr. 13, 2012.

* cited by examiner

FLANGED GRAFT WITH TRIM LINES

PRIORITY

This application claims the benefit under 35 U.S.C. §119 (e) to U.S. Provisional Application No. 60/695,406, filed Jul. 1, 2005, which is incorporated by reference into this application as if fully set forth herein.

BACKGROUND OF THE INVENTION

The use of vascular grafts for bypassing peripheral vascular occlusive conditions is believed to be well known, as is the use of microporous expanded polytetrafluoroethylene (ePTFE) in prosthetic vascular grafts. U.S. Pat. No. 6,436,135 to Goldfarb shows and describes an ePTFE prosthetic vascular graft; U.S. Pat. No. 6,273,912 to Scholz et al. shows and describes a flanged graft for end-to-side anastomosis; U.S. Pat. No. 6,190,590 to Randall et al. shows and describes an apparatus and method for making flanged grafts for end-to-side anastomosis; and the publication entitled, "Venaflo™ Vascular Grafts, Information for Use" shows an ePTFE graft with a modified venous end, each of which is incorporated by reference into this application as if fully set forth herein.

In current clinical practice, a peripheral anastomosis between a bypass prosthesis and a peripheral artery has been performed by either direct anastomosis, interposition of a venous segment at the anastomotic site, anastomosing the prosthesis with a long venous patch sutured into the artery, enlargement of the prosthesis with the anastomotic region using a venous patch, or interposition of a venous cylinder between the prosthesis and the artery. In bypass grafting, it is believed that hemodynamic factors are a major cause of thrombosis and the development of subintimal hyperplasia at the anastomotic site. In particular, hemodynamic phenomena may induce the development of intimal hyperplasia, e.g., occlusive legions that are predominately located at a venous anastomosis, which is believed to adversely affect the longevity of ePTFE grafts. Disturbed flow patterns, e.g., recirculation zones, flow separation and reattachment, development of stagnation points, and the rate of change of shear stress can be amplified due to abnormally high flow rates present in arteriovenous grafts. In the paper entitled "The Importance of Correct Trimming of Venaflo Graft Proven by CFD," presented at the 4th International Congress of the Vascular Access Society, May 25th to 27, 2005, Berlin, Germany, which is hereby incorporated by reference into this application, Dr. Ulf Krueger describes how graft geometry at the site of a venous anastomosis directly affects hemodynamic factors.

In order to mitigate intimal hyperplasia in an arteriovenous graft, it is known to use a bulb-like shape of the venous end-to-side anastomosis. Preferably, this includes a prefabricated cuff, which is attached to the venous anastomosis, resulting in an enlargement of anastomotic room with a curved vein floor. Flow studies related to the known vascular grafts are believed to suggest that blood flow patterns are optimized compared with previously known non-vascular grafts. However, the positive properties are closely connected with the correct design of the venous anastomosis. The hemodynamic is determined by the anastomotic metrics. Hence, the size and shape of the cuff must closely match the vein diameter in order to realize the aforementioned benefits. The prefabricated cuff, according to the known device, is only roughcast and may be trimmed relative to the vein diameter at maximal dilation by a clinician during surgery. However, if a graft is not trimmed precisely, sub-optimal results may occur.

Leonard Pinchuk, et al., U.S. Pat. No. 4,872,455 (Oct. 10, 1989), shows an anastomosis trimming device that is used for trimming a section of a tubular structure, such as a blood vessel or vascular graft, which is to be anastomosed, to provide an anastomotic end with a smooth, reproducible shape. That is, Pinchuk shows and describes a tool to specifically cut a middle or tubular portion of a graft instead of a flanged or cuffed end of a vascular graft.

Applicants have recognized that precise trimming of a prefabricated flanged end or cuff to achieve optimal blood flow patterns through the cuff can be accomplished through detailed instructions, including trim lines disposed on the cuff and/or through the use of tailoring devices.

BRIEF SUMMARY OF THE INVENTION

Accordingly, described herein is a vascular graft configured to offer optimal geometry for the anastomosis as a function of hemodynamic properties. By optimizing blood flow from the bypass prosthesis to the artery, it is believed that formation of intimal hyperplasia may be reduced with a concomitant increase in graft patency and decreased morbidity.

In one embodiment, the vascular graft includes a generally tubular member and an outwardly flared skirt or cuff that extends circumferentially about the tubular member, the cuff having trim lines and/or sizing indicia thereon. The trim lines indicate the precise size and shape for a cuff, depending on the target vessel to which it is to be attached. Precise trimming along the indicated markings provided directly on the cuff, or on a template to be positioned over the cuff, is believed to result in beneficial blood flow through the vascular graft. In another embodiment, an apparatus for precise trimming of a cuff is described, in which the apparatus includes a base that receives a vascular graft and a template that engages the cuff to guide a surgeon or clinician in trimming a peripheral edge of the cuff according to the size of blood vessel for which the graft is to be attached.

In one embodiment, a vascular graft includes a generally tubular member and a cuff extending from one end of the tubular member, the cuff including an open end spaced from the tubular member, the open end defining an initial outer perimeter having a shape, and a first marking disposed on a surface of the cuff spaced from the open end, the first marking providing an indication for trimming the cuff to a trimmed outer perimeter having a shape different than the shape of the initial outer perimeter.

In another embodiment, a template for a cuff of a vascular graft includes a section of material having a shape of at least a portion of the cuff with an adhesive disposed on a first side thereof and a plurality of markings on a second side thereof, the markings comprising a first trim line and a second trim line spaced from the first trim line. In yet another embodiment, a template for a cuff of a vascular graft includes a pocket including a first side joined to a second side along opposing edges thereof, one of the first side or second side including a first trim line.

In one embodiment, a trimming apparatus includes a base, including a mandrel having a tubular section and a flared section, and a template pivotally attached to the base, including an opening having a configuration of a cuff. In another embodiment, an apparatus is provided for trimming a vascular graft suitable for end-to-side anastomosis, the vascular graft including a tubular member and a flared skirt that projects from an end of the tubular member to a formed peripheral edge, the apparatus including a base that receives a portion of the flared skirt of the vascular graft, and a template that projects onto the flared skirt of the vascular graft a guide defining a trimmed peripheral edge of the flared skirt.

In another embodiment, a trimming guide is provided for a vascular graft suitable for end-to-side anastomosis, the vascular graft including a tubular member and a flared skirt, the tubular member having at least one alignment mark extending longitudinally between proximal and distal ends, and the flared skirt projecting from the distal end of the tubular member to a formed peripheral edge, the trimming guide including a first portion being registered with respect to the at least one alignment mark of the tubular member, and a second portion imposing on the flared skirt a guide that defines a trimmed peripheral edge of the flared skirt.

In yet another embodiment, a system of trimming a vascular graft suitable for end-to-side anastomosis is provided, the vascular graft including a tubular member and a flared skirt, the tubular member having a central axis extending between proximal and distal ends, and the flared skirt projecting from the distal end of the tubular member to a formed peripheral edge, the system including a base being registered with respect to the vascular graft, the base including a body engaging the flared skirt and a template imposing on the flared skirt a guide defining a trimmed peripheral edge of the flared skirt, and a cutting implement following the guide to define the trimmed peripheral edge of the flared skirt.

In one embodiment, a method of trimming a vascular graft suitable for end-to-side anastomosis is provided, the vascular graft including a tubular member and a flared skirt that projects from an end of the tubular member to a formed peripheral edge, the method including registering a guide with respect to the vascular graft, projecting the guide on the flared skirt of the vascular graft to define a trimmed peripheral edge of the flared skirt, and cutting the flared skirt to provide the trimmed peripheral edge.

In another embodiment, a method of trimming a vascular graft is provided where the graft has a generally tubular body that defines a longitudinal axis extending through the generally tubular body. The method can be achieved by providing a flared end connected to the generally tubular body; and cutting the flared end along a trimmed perimeter smaller than a generally elliptical boundary having two foci on a common axis, the trimmed perimeter defining a border contiguous to the generally elliptical boundary at a first location disposed on the common axis and at two locations disposed generally symmetrically about the common axis.

In yet another embodiment, a method of attaching a graft to a vessel includes providing a graft, including a tubular portion and a cuff portion extending from the tubular portion, the cuff portion including a first line and a second line disposed on a surface thereof, the first and second lines having the general shape of a peripheral edge of the cuff and being spaced apart from one another, and determining whether to trim the graft along one of the first and second lines based on the size of the vessel.

In one embodiment, a kit for producing a tailored graft, includes a vascular graft having a generally tubular body and an end section, and a tailoring apparatus selected from one or more of: a film having a shape of at least a portion of the end section with an adhesive disposed on a first side thereof and a plurality of markings on a second side thereof, a pocket including a first side joined to a second side along opposing edges thereof, one of the first side or second side including one or more tailoring lines; a cutting device including a base configured to engage the end section, a template defining a tailoring perimeter, and a cutting implement positioned along the tailoring perimeter; and, a trimming device including a mandrel with a tubular section and a flared section, and a template with an opening shaped in the form of a predetermined shape for the end section, the opening including a cutting edge along a perimeter thereof.

These and other embodiments, features and advantages will become apparent to those skilled in the art when taken with reference to the following more detailed description of the invention in conjunction with the accompanying drawings that are first briefly described.

DETAILED DESCRIPTION OF THE PREFERRED EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
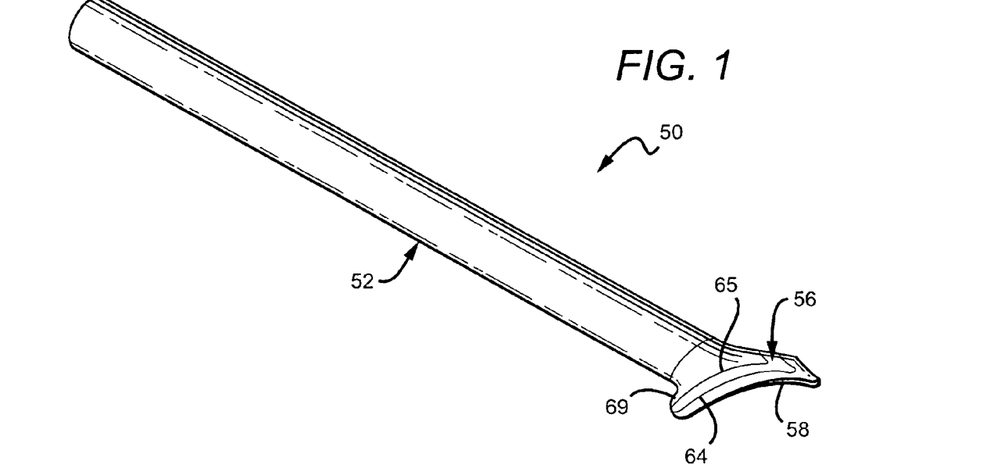
FIG. 1 is a perspective view of one embodiment of a vascular cuff graft with trim lines.
Figure 2:
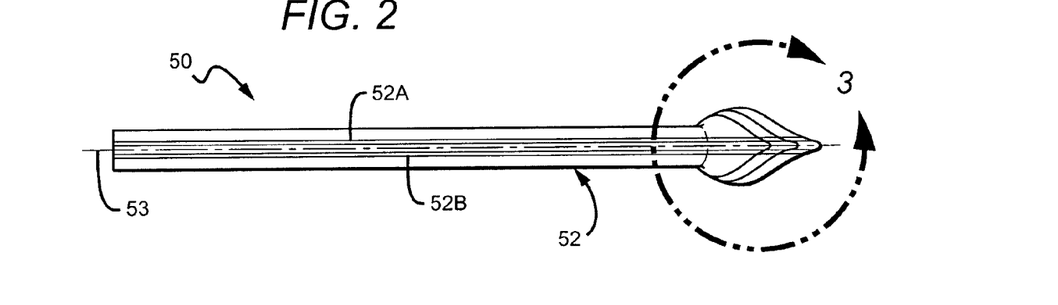
FIG. 2 is a top view of the vascular cuff graft of FIG. 1
Figure 3:
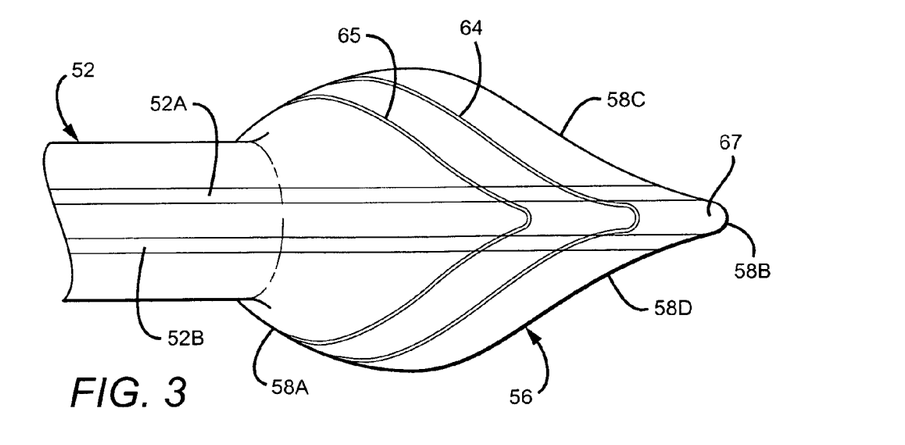
FIG. 3 is an enlarged view of the cuff of the vascular cuff graft shown in FIG. 2.

One embodiment of a vascular cuff graft is illustrated in FIGS. 1-3. Vascular cuff graft 50 includes a tubular member 52 and an outwardly flared skirt or cuff 56 extending from one end of the tubular member 52. The cuff 56 is offset from the longitudinal axis 53 such that one focal point of the cuff is positioned a greater distance from the longitudinal axis 53 than another focal point of the cuff. The cuff 56 includes a toe section 67, which projects away from the tubular member 52 in one direction, and a heel section 69, which projects away from the tubular member 52 in the opposite direction.

The cuff 56 in the embodiment shown in FIGS. 1-3 is continuous and integral with the tubular member 52, without any intervening seams or overlap. The tubular member 52 and/or cuff 56 may be formed from a suitable biocompatible material such as, for example, from polytetrafluoroethylene, polyester, polyurethane, or fluoropolymers, such as perfluoroelastomers, and combinations thereof; however, in the preferred embodiment, ePTFE is used to form the tubular member 52 and cuff 56. The thickness of vascular graft 50 in one embodiment is approximately 0.9 mm and can vary along the length of the graft. Preferably, the vascular graft 50 is thinner at the cuff 56 and thicker along the tubular member 52. According to preferred embodiments, a coiled beading made of PTFE may be helically wound about an outer surface of the tubular member 52 to reduce kinking. The beading can be impregnated with a radiopaque material, such as barium sulfate or hydroxyapatite, to increase visibility under radio imaging (e.g., x-ray).

Bioactive agents may be incorporated into the vascular cuff graft 50, including, but not limited to, activated charcoal, carbon particles, graphite particles, vasodilator, anti-coagulants, such as, for example, warfarin and heparin. Other bioactive agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) II$_b$/III$_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The vascular cuff graft 50 may include an alignment guide that is printed or otherwise marked on an outer surface of the tubular member 52. The alignment guide in the embodiment shown in FIGS. 1-3 includes a pair of lines 52A and 52B, which extend generally parallel to a central longitudinal axis 53 of the vascular cuff graft 50. In other embodiments, the alignment guide may include one line or three or more lines, or may include a different type of marking. The alignment guide may extend onto the cuff 56 as shown in FIGS. 1-3. As shown in the enlarged view of FIG. 3, the cuff 56 has an edge 58 defining an outer perimeter, including opposing convex portions 58A, 58B and opposing concave portions 58C, 58D. The edge 58 in a preferred embodiment is an edge previously trimmed by a vascular surgeon from a conventional elliptically-shaped cuff prior to attachment to a vessel, as explained below in connection with FIGS. 6A-6B.

Markings, such as trim lines 64 and 65, are positioned on a top surface of the cuff 56 to provide alternatives to a vascular surgeon for tailoring the size of the cuff 56, depending on the vessel to which it is to be attached. In the embodiment shown in FIGS. 1-3, the trim lines 64 and 65 are spaced from one another and generally follow the shape of the edge 58 of the cuff 56 (i.e., the trim lines 64, 65 and the edge 58 are generally parallel to one another). The shape of the edge 58, as mentioned, is different from the elliptical shape of the perimeter of a conventional bulb-like cuff from which it is preferably cut. However, in other embodiments, each of the trim lines may be positioned on a surface of the cuff in patterns different from one another such that the surgeon may choose a different shape for the cuff depending on a particular need. The trim lines 64, 65 may be solid or dashed (see FIG. 5A). The trim lines 64, 65 (and peripheral edge 58 prior to trimming) permit a vascular surgeon to tailor the cuff 56 to a specific size or shape determined during an implant procedure to accommodate the open arteriotomy at an anastomotic site. The trim lines and other indicia may be printed on a surface of the cuff 56 using inks as described below.

Preferred formulations for inks provide different colors. For example, a bright cobalt blue line at 33% urethane is provided by dissolving three grams urethane in 17 grams THF (a 12% solution is preferable), then mixing in 1.0 grams cobalt blue. A dark blue line that is an FDA safe mixture includes FD&C #2 at 1% of urethane and cobalt blue at 2% urethane, which is provided by dissolving 0.3 grams FD&C #2 in 15 grams of water and heating to approximately 150 degrees C.; adding 20 grams of DMAc to the water solution, making an azeotrope, and shaking well; adding 15 grams of urethane to 85 grams of THF and dissolving thoroughly (15% solution); adding 3.5 grams of the DMAc water solution to the 100 grams of the urethane/THF solution; and adding 0.3 grams cobalt blue to the resulting solution and shaking well. Commercially available inks may also be used. For example, TPR Ink manufactured by Marabuwerke GmbH & Co. (Tamm, Germany), is available from Autoroll Print Technologies, LLC (Middleton, Mass.; part number 3803 57 980). As a thinner for the TPR Ink, TPV Thinner, also manufactured by Marabuwerke GmbH & Co., is also available from Autoroll Print Technologies, LLC (part number 3501 97 046). Also, TPU ink, manufactured by Marabuwerke GmbH & Co., may be used.

Figures 4, 5A, 5B:
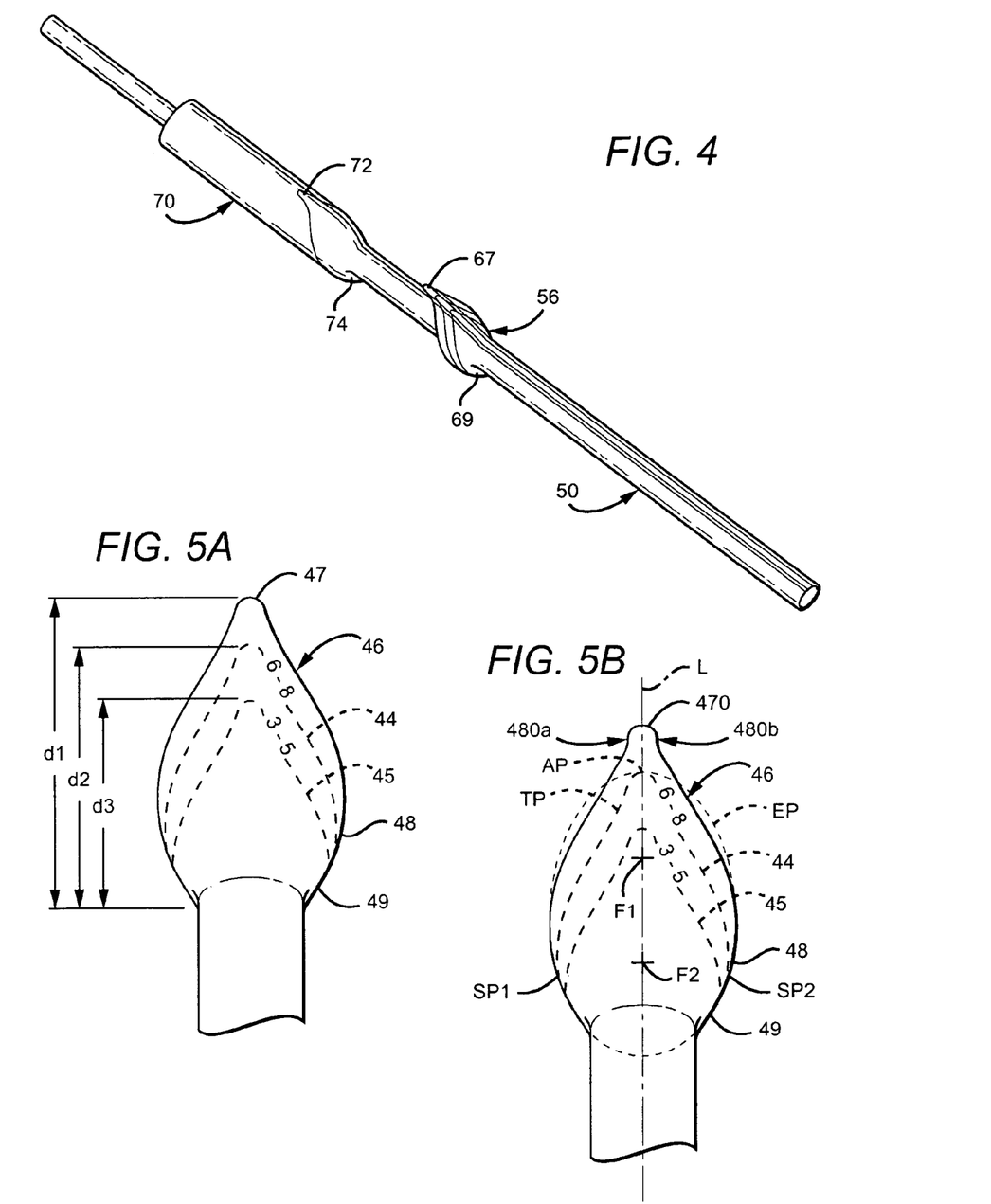
FIG. 4 is a perspective view of the vascular cuff graft of FIG. 1 disposed over a section of a mold.
FIG. 5A is a top view of another embodiment of a vascular cuff graft with trim lines.
FIG. 5B is a top view of another embodiment of a vascular cuff graft with trim lines.

An integral cuff 56 may be formed, for example, by any of a variety of methods known to one skilled in the art, such as, for example, using the apparatus and method described in U.S. Pat. No. 6,190,590 to Randall et al. Referring to FIG. 4, one preferred method of forming a vascular cuff graft 50 includes selectively expanding a section of an ePTFE tube using a mold 70. The mold 70 may include specific contours that correspond to a cuff, such as cuff 56. For example, the toe section 67 of the cuff 56 corresponds to a toe contour 72 of mold 70 and the heel section 69 of the cuff 56 corresponds to a heel contour of the mold 70. In another embodiment, the cuff 56 could be separately formed and attached to the tubular member 52 using methods known to one skilled in the art (e.g., suture, heat, adhesives, etc.).

In addition to trim lines on a surface thereof, the cuff may include printed indicia as shown in FIG. 5A on a cuff 46. Cuff 46 is similar to cuff 56 but which could include a toe 47 that is more pointed than toe 67. In the example shown, the printed indicia on cuff 46 is in line with trim lines 44, 45 to indicate to a surgeon the diameter size of the vein or vessel for each line. As with edge 58 of cuff 56, the edge 48 defining a perimeter of cuff 46 is preferably an edge previously trimmed by a vascular surgeon from a conventionally-shaped cuff prior to attachment to a vessel, as described below. The sizing along the outer peripheral edge 48 is designed for a vessel having a diameter from approximately 9 mm to approximately 10 mm (and may previously had numerical indicia associated therewith (e.g., "9-10") prior to trimming). Trim line 44 includes numerical indicia "6-8" to indicate that the surgeon should trim the cuff 46 along line 44 if the vessel is from approximately 6 mm to approximately 8 mm. Trim line 45 includes numerical indicia "3-5" to indicate that the surgeon should trim the cuff 46 along line 45 if the native vessel is from approximately 3 mm to approximately 5 mm. The numerical indicia in this embodiment is positioned in-line with the trim lines 44, 45; however, in other embodiments, the numerical indicia can be adjacent the trim line along any section thereof. The lengths of the cuff 22 or distance between heel and toe, depending on the trim line chosen in this embodiment are as follows: the distance $d_1$ between the heel 49 and toe 47 in the cuff 46 trimmed along outer peripheral edge 48 is approximately 30 mm; the distance $d_2$ between the heel and toe on the cuff trimmed along line 44 is approximately 25 mm; and the distance $d_3$ between the heel and toe on the cuff trimmed along line 45 is approximately 20 mm.

By virtue of the various embodiments described herein, a method of trimming a vascular graft is realized. In such method, the graft has a generally tubular body that defines a longitudinal axis extending through the generally tubular body. The method can be achieved by providing a flared end connected to the generally tubular body, shown here in FIG. 5B, and cutting the flared end along a trimmed perimeter smaller than a generally elliptical boundary having two foci on a common axis. As shown in FIG. 5B, the flared end or cuff 46 is precut to a first configuration for native vessel larger than 8 mm so that a clinician is not required to trim the graft for optimum hemodynamic characteristics. It is noted that, in this embodiment, the toe 470 is different that the toe 47 of FIG. 5A in that the toe 470 is connected to the graft via generally linear portions 470a and 470b. For vessel 8 mm or smaller, trim lines 44 and 45 are provided. Each trim line has an apex located generally on a common axis of a virtual generally elliptical boundary EP. For example, trim line 44 has apex AP located generally on the common axis L (which, coincidentally, in the view of FIG. 5B, the longitudinal axis 53 and common axis L are on axis) as defined by the foci F1 and F2 of the virtual ellipse boundary EP. Upon trimming along the line 44 by a clinician, a trimmed perimeter TP is provided that defines a border 44 (dashed lines) contiguous to the generally elliptical boundary EP at a first location disposed on the common axis L, e.g., AP and at least two other locations SP1 and SP2 disposed generally symmetrically about the common axis L. And the first location (at apex AP) may include a farthest terminal end of the vascular graft once the cuff has been trimmed. In such method, the flared end can be a separate member or it can be an integral and monolithic part of the generally tubular body.

As discussed above, known vascular grafts with a bulbous-like flange or cuff are believed to lead to an enlargement of anastomotic room with a curved vein floor when attached to a vein in an end-to-side anastomotic procedure. Simulated flow studies related to these cuff grafts suggest that blood flow patterns are optimized in comparison to other prior grafts. However, the positive properties associated with the cuff graft are closely tied to the correct design of the venous anastomosis. Regardless of the manufactured size and shape, the cuff generally must be trimmed somewhat prior to attachment to a vein. However, even in instances when trimming instructions are provided, if the trimming advice is not followed exactly and the cuff not trimmed precisely on the dotted lines or markings indicated, there is believed to be an increased risk of sub-optimal results, one of which is the formation of a hooded region proximate the attachment point of the toe.

Figures 6A, 6B, 7A, 7B:
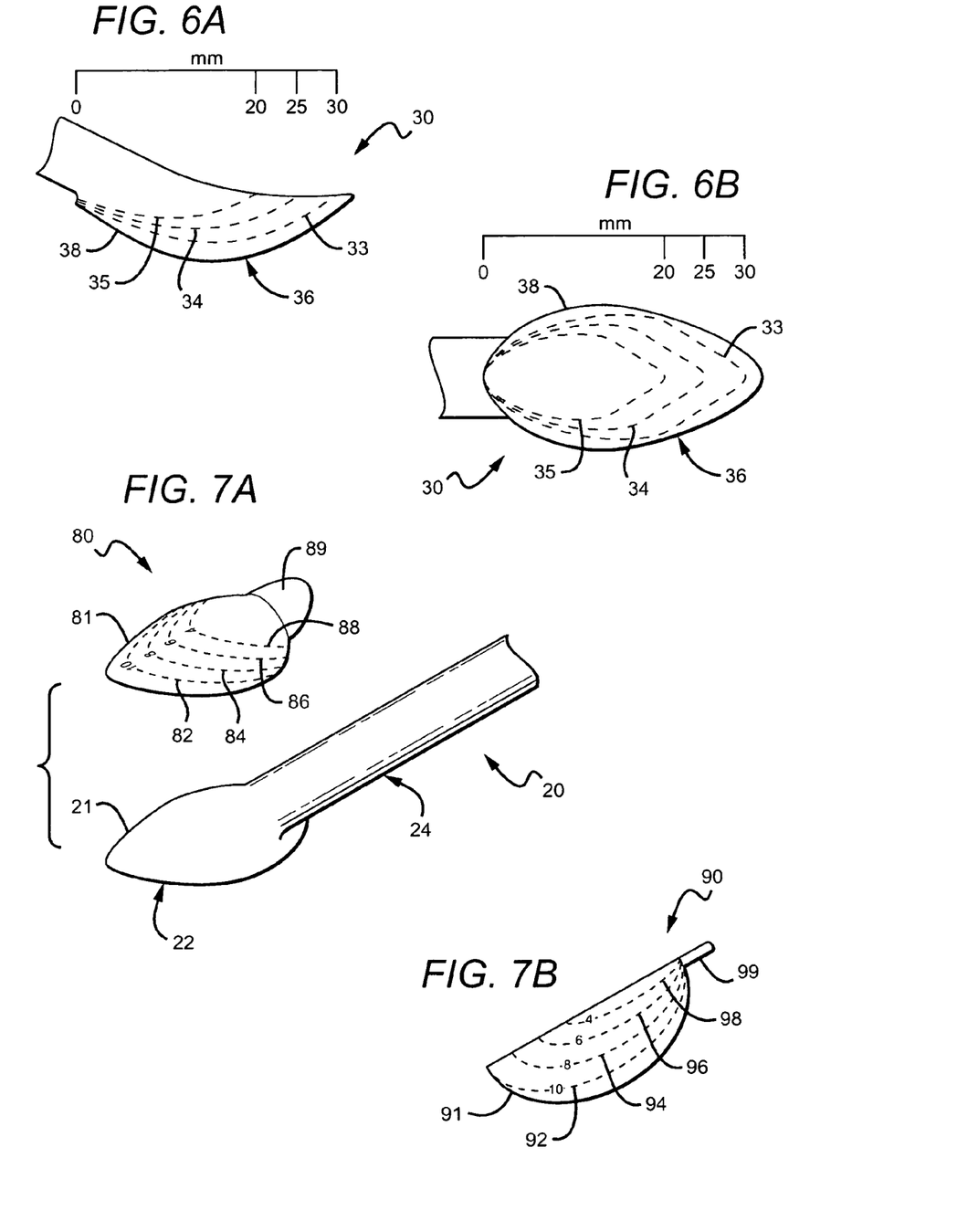
FIG. 6A is a side view of another embodiment of a vascular cuff graft with trim lines.
FIG. 6B is a top view of the vascular cuff graft of FIG. 6A.
FIG. 7A is one embodiment of a template for disposition over a cuff of a vascular cuff graft.
FIG. 7B is another embodiment of a template for disposition over a cuff of a vascular cuff graft.

FIGS. 6A and 6B show a preferred embodiment of a cuff graft 30 to address this potential problem. Cuff graft 30 is shown with three trim lines 33, 34, 35 on a surface of a cuff 36 spaced approximately 5 mm from each other as depicted. Of course, the intervals between trim lines can be greater or less than 5 mm and the distances between trim lines can also be varied. The outer periphery 38 of the cuff 36 has a conventional bulb-like form, but is not intended for use. Instead, as shown in FIG. 6B, a modified trim pattern for each of the trim lines 33, 34, 35 is provided. In this embodiment, the distance between the heel and the toe on the cuff trimmed along line 33 is approximately 30 mm; the distance between the heel and toe on the cuff trimmed along line 34 is approximately 25 mm; and the distance between the heel and toe on the cuff trimmed along line 35 is approximately 20 mm.

Referring back to FIGS. 1-5, perimeter edges 48, 58 of cuffs 46, 56 are preferably trim lines on a preferred vascular graft prior to trimming by a surgeon. Where the native vessel is greater than 8 mm, no trimming is needed due to the pre-configured perimeter edge 48. Where the native vessel is from approximately 6 mm to approximately 8 mm, trim edge 44 is provided (e.g., printed) on the cuff end of the graft. Where the native vessel is from approximately 3 mm to approximately 5 millimeter, trim edge guide 45 is provided (e.g., printed) on the cuff of the graft.

The study presented in the paper entitled "The Importance of Correct Trimming of Venaflo Graft Proven by CFD," presented at the 4th International Congress of the Vascular Access Society, May 25th to 27, 2005, Berlin, Germany, describes how graft geometry at the site of a venous anastomosis directly affects hemodynamic factors. In particular, the study found that the precise trimming of a cuff along modified lines, such as lines 33, 34 and 35 in cuff graft 30, and particularly in predefined perimeters 44, 45, and 46 resulted in measurable advantages over cuff grafts with untrimmed conventional bulb-like cuff configurations and/or cuffs that were not precisely trimmed according to the vein diameter at maximum dilation of the target vein. Such advantages include an enlarged anastomotic room, leading to durable flow separation and a prolonged three-dimensional vortex with clockwise rotation, a reduction of pressure rise due to fluid stagnation at the vein floor, and reduced shear stress on the vein floor (which is believed to lead to delayed, reduced or elimination of intimal hyperplasia and venous anastomotic stenosis). Thus, it is believed that precise trimming of a cuff graft, according to the particular perimeter shown and described herein, imparts surprising benefits to the cuff graft at least with respect to the advantages mentioned.

In another embodiment, rather than printing indicia and/or trim lines on a surface of the cuff of a cuff graft, a sizing template may be provided for a conventional cuff graft to enable precise trimming of the cuff to achieve the advantages discussed above. FIG. 7A illustrates one embodiment of a sizing template 80 configured to be positioned over a bulb-like cuff 22 of a conventional cuff graft 20. In one embodiment, the template 80 is a section of material, such as a film, with adhesive disposed on one side. On the non-adhesive side of the template 80, markings, such as trim lines, indicia, etc., are disposed to aid a vascular surgeon in precise trimming of the graft. In the embodiment shown, the film is a clear/transparent plastic having pre-printed markings; however in other embodiments, the film or like material may be translucent or partially transparent and partially translucent.

As shown in FIG. 7, the template 80 may have four trim lines, 82, 84, 86, 88, for sizing the cuff 22 to a different diameter vessel when trimmed along the trim lines. Thus, in the example shown, for a vessel having a maximum dilation of 10 mm, the vascular surgeon would trim along trim line 82 following attachment of the template 80 to the cuff 22. Likewise, for a vessel having a maximum dilation of 8 mm, 6 mm and 4 mm, the surgeon would trim along lines 84, 86 and 88, respectively. The peripheral edge 81 of template 80 in the preferred embodiment is shaped substantially similar to the cuff on which it is to be placed so that the edge 81 of the template 80 can be matched with the edge 21 of the cuff 20 to ensure precise trimming of the cuff 20. Also, in the embodiment shown, template 80 includes a tab 89 without an adhesive backing in order to facilitate removal of the template 80 following the trimming procedure.

The template 80 may be positioned over a cuff prior to packaging and sold together as a unit, or may be packaged separately from a cuff such that it must be placed over the cuff prior to trimming by a surgeon as described above. In one embodiment, the template 80 is halved such that it is configured to be placed over only a portion of the cuff 22. Thus, the cuff 22 is first folded in half along a line of symmetry prior to attaching a half-sized template 90 with adhesive backing, shown in FIG. 7B, to one half of the cuff 22. As with the full-size template 80, template 90 includes a peripheral edge 91 to match the peripheral edge of the folded-in-half cuff 22, and four trim lines 92, 94, 96, 98, for sizing the cuff 22 to a different diameter vessel when trimmed along the trim lines. The template 90 may also include a tab 99 without adhesive backing. While four trim lines are indicated in FIGS. 7A and 7B, it should be appreciated that the templates 80, 90 could have less than four trim lines or more than four trim lines with each trim line being indicated for a different diameter target vessel.

Figure 8:
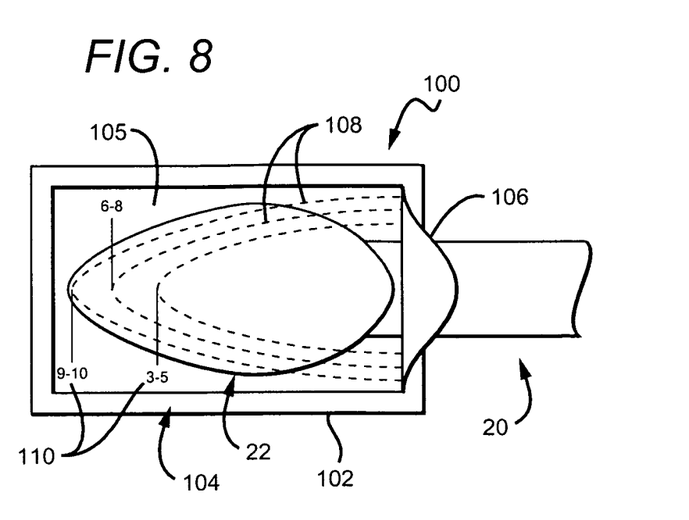
FIG. 8 is one embodiment of a pocket template into which a cuff of a vascular graft is disposed.

In another embodiment, shown in FIG. 8, a pocket 100 is provided for housing a cuff 22 of a cuff graft 20. The pocket 100 may be formed of two overlying sheets of film 104 with peripheral edges 102 that are configured to be coupled together to form a void in which the cuff 22 is disposed. The edges 102 may have adhesive disposed on one side thereof or may be otherwise coupled together by methods known to one skilled in the art (e.g., heat, chemical bonding, etc.). Alternatively, the pocket 100 may be formed of a single sheet of film folded along a symmetry line, having edges configured for coupling as discussed. The coupling of the sheets of film 104 (or sheet) along peripheral edges 102 may be continuous or intermittent, although it is preferred that the pocket 100 be sealed along the edges 102 except for the portion through which the cuff graft is positioned. The sheet or sheets of film 104 include at least one side with a clear or transparent face 105 such that the cuff 22 can be viewed by a user. The face 105 includes a template with trim lines 108 and/or indicia 110 to guide a surgeon in the trimming of the cuff 22 based on the diameter of the vessel to which it is to be attached, as discussed above. It is noted that the face 105 of both sides of the pocket 100 may include a template with trim lines 108 and/or indicia 110, such that the cuff may be inserted or positioned with the top surface adjacent either face 105.

Opposing tabs 106, each positioned on one side of an inserted cuff graft 20, are provided on the pocket 100 to facilitate removal of the pocket 100 following the trimming of the cuff 22. In the embodiment shown, the pocket 100 is rectangular; however, the pocket may be in any shape including the shape of the cuff 22. The pocket 100 may be positioned over a cuff 22 of a cuff graft 20 and sold as a unit, or may be sold or packaged separately for assembly by an end user. When sold as a unit, the cuff 22 is secured within the pocket 100 such that cutting along the trim lines results in an optimal size and shape of the cuff 22 for attaching to a blood vessel of desired size. The cuff 22 may be secured, for example, by shrinking slightly the material of the pocket 100, by sizing the pocket 100 slightly smaller than the cuff 22 so that the toe and side edge are sealed into the edges of the pocket 100, by applying a thin coat of medical grade lubricant to the inside of the pocket in order to contact the top of the cuff to adhere the cuff 22 to the pocket 100, or other methods known to one skilled in the art. In another embodiment, a half-sized pocket is provided to accommodate a cuff 22 that has been folded along a line of symmetry. This pocket would have partial markings, including a template with trim lines and/or indicia, similar to the half-sized template described above.

Figure 9:
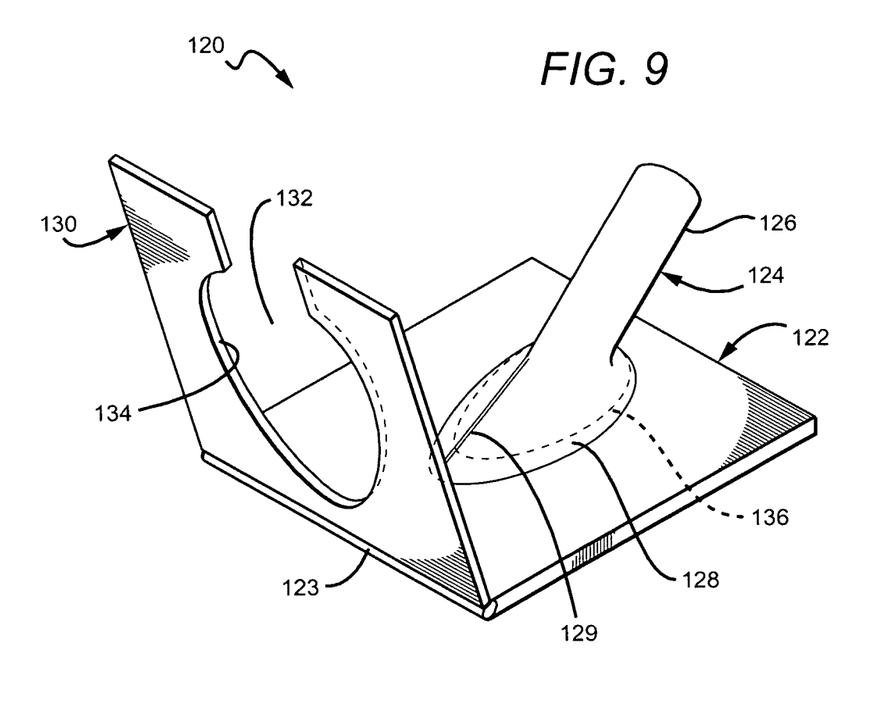
FIG. 9 is one embodiment of a trimming apparatus used to facilitate and ensure precise trimming of a cuff of a vascular graft.

In another embodiment illustrated in FIG. 9, a trimming apparatus 120 is provided to ensure precise trimming of the cuff 22 of a cuff graft 20 to achieve desired advantages. The trimming apparatus 120 includes a base 122, including a mandrel 124 shaped to receive a cuff graft 20 thereover, the mandrel 124 having a tubular section 126 and a flared section 128 shaped to correspond to the tubular section and cuff section of a cuff graft (e.g., the flared section 128 includes a heel section and a toe section to correspond to a heel and toe of a cuff). In one embodiment, the mandrel 124 has disposed thereon a register, which may be a pair of lines 129 positioned on the flared section 128 to correspond to the alignment guide 24 on the cuff graft 20, such that the proper positioning of the cuff graft 20 onto the mandrel 124 is both facilitated and ensured. In other embodiments, the register may be one or more features such as markings, mating shapes, etc., to ensure proper positioning of the cuff graft 20 so that precise trimming of the cuff 22 is achieved and to facilitate the process.

Pivotally attached (e.g., via a hinge, etc.) to the base 122 along an edge 123 adjacent a toe portion of the flared section 128 is a template 130. The template 130 includes an opening 132 configured in the desired pattern for a cuff of a cuff graft to achieve optimal flow conditions for a particular diameter vessel, as discussed above. Thus, in one embodiment, the opening 132 includes a section with opposing convex portions to create opposing concave portions on the cuff 22 of a cuff graft 20 positioned over the mandrel 124 (e.g., FIG. 6B). When the template 130 is pivoted toward the mandrel 124, following the positioning of a cuff graft 20 thereover, the edge 134 of the opening 132 engages the cuff 22 of a cuff graft 20 placed over the mandrel 124 generally along the area depicted by dotted line 136. In one embodiment, the edge 134 includes a sharp cutting blade or surface, such that engagement with the cuff 22 results in the trimming thereof according to the outline of the edge 134. In other embodiments, the edge 134 is blunt and engagement with the cuff 22 provides an outline along which the surgeon or clinician can trim, either while the edge 134 of the template 130 is engaged with the cuff 22 or by creating an impression on the cuff to guide the trimming thereof after the template 130 is pivoted away therefrom.

In the example shown in FIG. 9, the outline of the edge 134 is for a large diameter vessel (e.g., 9-10 mm), such that trimming for smaller vessels can take place, in one embodiment, through the use of one or more separate cutout members that mate with the opening 132 and are nested therein. For example, a cutout member for the trimming of a cuff 22 for attachment to a 6 mm diameter vessel would have an inside edge corresponding to the optimal shape and size of a cuff therefore and an outside edge to mate with edge 134. The cutout member could be attached to the opening 132 via one or more locking mechanisms or detachable connections (e.g., snap fit, latch, Velcro, etc.) prior to pivoting over the cuff 22. The cutout members could either have a sharp cutting blade or surface to trim upon engagement with the cuff 22 or have a blunt edge to permit trimming of the cuff 22 by the surgeon or clinician, as discussed above.

In another embodiment, the opening 132 is adjustable, depending on the size and shape desired. For example, the opening 132 may include an adjustable edge or surface that can be slid or moved into a desired position depending on the diameter of the vessel to which the cuff 22 is to be attached. Settings could be provided for each of a number of different diameter vessels and each setting could include a locking mechanism. For example, the opening 132 may have an adjustable edge with settings for a 3-5 mm diameter vessel and a 6-8 diameter vessel, assuming that the original opening 132 is configured to correspond to an optimal shape and size for attaching to a 9-10 diameter vessel. Thus, to adjust the edge for a smaller diameter vessel, a locking pin or like mechanism could be adjusted to move the edge inward. The adjustable edge could include numeric indicia on a surface thereof to indicate to a user the diameter of vessel for each setting. In one embodiment, the cutout member is adjustable to provide the ability to trim to several different sizes and shapes of cuffs based on need, the cutout member having an outside surface and contour that mates with the inside surface of the opening 132, and an inside surface that can be adjusted to different shapes and/or sizes.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed as new and desired to be protected by Letters Patent of the United States is:

1. A vascular graft, comprising:
a generally tubular member and a cuff extending from one end of the tubular member, the cuff including an open end spaced from the tubular member, the open end defining an initial outer perimeter having a generally elliptical shape;
a first marking disposed on a surface of the cuff spaced from the open end, the first marking providing an indication for trimming the cuff to a trimmed outer perimeter having a toe section with opposing concave portions and opposing convex portions; and
an alignment guide disposed on a surface of the tubular member and the cuff, the alignment guide including first and second lines generally parallel to each other and to a longitudinal axis of the tubular member, the alignment guide intersecting the first marking.

2. The vascular graft according to claim 1, wherein the cuff is integral and continuous with the tubular member.

3. The vascular graft according to claim 1, wherein the cuff is offset from a longitudinal axis of the tubular member such that a first focal point of the cuff is positioned a greater distance from the longitudinal axis than a second focal point of the cuff.

4. The vascular graft according to claim 3, wherein the cuff includes a toe section adjacent the first focal point and a heel section adjacent the second focal point.

5. The vascular graft according to claim 1, wherein the toe includes a pointed tip.

6. The vascular graft according to claim 1, wherein the first marking comprises a first trim line extending around a circumference of the cuff.

7. The vascular graft according to claim 6, further comprising a numerical indicia positioned adjacent a section of the first trim line.

8. The vascular graft according to claim 1, further comprising a second marking spaced from the first marking, wherein the first and second markings comprise first and second trim lines and wherein the first and second trim lines are generally parallel to one another.

9. The vascular graft according to claim 8, further comprising a third marking spaced from the second marking, wherein the third marking is a third trim line generally parallel to the first and second trim lines.

10. The vascular graft according to claim 9, further comprising a numerical indicia positioned adjacent a section of each of the first, second and third trim lines.

11. The vascular graft according to claim 10, wherein the numerical indicia adjacent a section of the first trim line is different from the numerical indicia adjacent a section of the second trim line, which is different from the numerical indicia adjacent a section of the third trim line.

12. The vascular graft according to claim 1, wherein the first marking comprises numerical indicia indicating an optimal range for the diameter of vessel to which the vascular graft is configured for attachment, and wherein the tubular member and cuff are comprised of expanded polytetrafluoroethylene.

13. The vascular graft according to claim 1, wherein at least one of bioactive agents and radiopaque material is disposed in the graft.

14. The vascular graft according to claim 1, wherein the first marking comprises a biocompatible blue ink.

* * * * *